United States Patent [19]

Buissiere

[11] 4,218,537

[45] Aug. 19, 1980

[54] MEDIUM FOR THE CULTIVATION OF MICROORGANISMS

[75] Inventor: Jean Buissiere, Paris, France

[73] Assignee: Institut Pasteur, Paris, France

[21] Appl. No.: 709,426

[22] Filed: Jul. 28, 1976

[30] Foreign Application Priority Data

Jul. 30, 1975 [FR] France ............................. 75 23851

[51] Int. Cl.$^2$ ............................................. C12Q 1/04
[52] U.S. Cl. ..................................... 435/34; 435/252; 435/253; 435/254; 435/801
[58] Field of Search ........ 195/100, 102, 126, 103.5 M; 435/252, 253, 254, 34, 801

[56] References Cited

U.S. PATENT DOCUMENTS

| 2,358,549 | 9/1944 | Wenck | 195/100 |
| 2,446,091 | 7/1948 | Humm | 195/100 |
| 3,046,201 | 7/1962 | White et al. | 195/100 |
| 3,067,109 | 11/1962 | Baron | 195/100 |
| 3,247,078 | 4/1966 | Hetnett | 195/102 |
| 3,553,148 | 1/1971 | Bourland | 195/100 |

OTHER PUBLICATIONS

Whistler et al., Industrial Gums, Academic Press, pp. 28, 29, 36, 37 & 46 (1959).
Difco Manual, p. 290 (1956).
Chemical Abstracts, vol. 46, 9660c (1952).
Hawley, The Chemical Dictionary, Eighth Ed., p. 714 (1971).

*Primary Examiner*—Alvin E. Tanenholtz
*Attorney, Agent, or Firm*—Weiser, Stapler & Spivak

[57] ABSTRACT

Base medium for the constitution of culture media for microorganisms.

It has a sufficient viscosity for strict aerobic microorganisms, even mobile, to be able to develop only at the surface or close to the latter, this viscosity however not exceeding that which would result in too great a decrease in fluidity, preventing sedimentation of microorganisms in this medium, under the effect of gravity.

Application to the characterization or to the identification of microorganisms.

6 Claims, No Drawings

MEDIUM FOR THE CULTIVATION OF MICROORGANISMS

The invention relates to a new basic medium intended to serve particularly for the constitution of culture media for the most diverse of microorganisms, which is capable of receiving the various elements of nutrition or nutriments necessary for the development of these microorganisms, and, if necessary, various agents which are expected to exert effects to be studied on this development; and it relates obviously also to the so constituted culture media.

It is known in fact that all microorganisms, for example, all bacterial species, cannot develop on the same culture media. It is expedient for each family, each genus, and sometimes for extremely closely related species, to define special culture media. In the same way, various substrates or agents introduced into these culture media, either encourage, or inhibit the development of a particular microorganism. Hence there has been an extreme diversity in the behaviour of microorganisms with respect to the numerous culture media which have been developed until now, whence are derived also the known techniques for the identification of families, of genii, even of particular species of microorganisms, or simply the verification of certain of their essential properties, which bring into play their aptitude for metabolising such nutriments in such media, if necessary in the presence of such particular chemical or biological agents.

These characterising or identification techniques are often difficult to put into practice by reason of the unsuitability of the base media used for the constitution of the culture media utilised until now, for the systematic and standardised practice of all the culture tests necessary for these identifications or characterisations.

For example, among the basic characteristics of these microorganisms, is to be found notably their capacity or incapacity to develop in the presence of oxygen. The latter constitutes, in fact, an essential nutriment, for example, for bacteria called "strict aerobic" bacteria, whilst it is ametabolic poison to bacteria called "strict anaerobic" bacteria. Between these extremes, are also found families of aero-anaerobic bacteria, which are capable of developing, both in the presence and in the absence of oxygen. In each of the above-mentioned categories, there are also to be distinguished sometimes, immobile or mobile microorganisms.

These culture media used hitherto, namely liquid culture media or solid culture media, do not enable "aerobic" microorganisms, "anaerobic" microorganisms and "aero-anaerobic" microorganisms to be distinguished rapidly in a single manipulation. In fact, the cultivation of anaerobic microorganisms in a liquid medium, even in depth, is not easy, by reason of the capacity of the ambient oxygen to diffuse into the midst of the liquid mass, unless it is carried out in an atmosphere devoid of oxygen. Furthermore, cultivation in liquid media will not always permit, notably under an oxygen atmosphere, differentiation to be made between strict aerobic microorganisms and aero-anaerobic microorganisms, taking into account the capacity of aerobic cultures to develop throughout the mass of the liquid culture. Conversely in the absence of external oxygen, differentiation will not be made between aero-anaerobic microorganisms and strict anaerobic microorganisms, taking into account the property of aero-anaerobic microorganisms to develop equally throughout the mass of the medium under such conditions.

Liquid media are certainly easy to manufacture (for example, by simple solution or suspension of the nutrient substances or the substances the metabolism of which is to be investigated and are also easy to inoculate with the microorganisms or the bacteria to be studied. However, as shown by the example above, the applications of liquid media are not always able to suffice for all the necessary operations of characterisation and/or of identification.

Solid media are therefore also still used currently in bacteriological laboratories, in spite of the inherent difficulties in their employment. In particular, coming back to the example already mentioned, it is observed that solid media permit identifications or characterisations which are difficult or impossible to put into practice in liquid media. Aerobic microorganisms only develop at their surface. Strict anaerobic microorganisms can be cultivated in the mass of the solid medium. Observation of the growth in the mass of the solidified medium also permits differentiation between strict aerobic microorganisms and aero-anaerobic microorganisms.

These solid media must however comply with numerous conditions. They must be essentially non-biodegradable and inert with regard to bacterial cultures. They must be transparent, capable of being brought into the liquefied state at relatively low temperatures, notably to permit their seeding with the strains of microorganisms to be cultivated and, at the same time, not be liquefiable at these same temperatures when they occur in the solid state.

In current practice, only gelose or agar gels enable these apparently conflicting conditions to be met. In fact, solid gelose gels which contain at least 10 g and generally of the order of 20 g of gelose per liter of water, have the property of melting at a temperature of the order of 100° C., so that these gels remain solid at all cultivation temperatures for microorganisms. However, after melting, these gels remain liquid until the temperature has dropped back to 35°–40° C., which makes it possible to seed them with the microorganisms to be cultured, without risk of killing them before re-gelling of the medium into an elastic and transparent gel. By reason of the difficulties which have just been mentioned, it is only very exceptionally that recourse is had for the preparation of solid media of strictly defined chemical composition, to very rare other gelling agents, such as, for example, silicic acid (whose gels are besides very delicate to prepare).

Hence, it has not been possible hitherto in practice, to obviate tedious manipulations involved in the necessary preliminary melting of gelose gels at a high temperature, and then their cooling under suitable conditions. At the most, it will be observed that the need for this melting at high temperature forbids the study of the effect on the growth of microorganisms of products which are decomposed by heat (vitamins, amino acids and certain macromolecules). This necessary melting also makes difficult, if not impossible, the use of plastics containers.

It is an object of the invention to overcome these various drawbacks, more particularly to provide basic media which can be substituted both for liquid media and for traditional solid media, which have hence the properties of solid media and of liquid media at the same time, whose manipulation is simple and which do not require any of the heat treatments which have been mentioned with respect to solid media.

The invention results from the discovery that the capacity of strict aerobic microorganisms to develop in the body of a liquid could be interrupted fairly rapidly by an increase in the viscosity of this liquid, notably the addition to the latter of controlled amounts of viscosity agents, the necessary viscosities being able to remain compatible with the preservation of sufficient fluidity to permit the sedimentation of microorganisms, even immobile, in the midst of the thus constituted medium, under the simple effect of gravity, as in a true liquid medium.

In conferring a certain viscosity on this liquid, it is hence achieved that strict aerobic microorganisms are only capable of developing or of growing at the surface or close to the latter.

This phenomenon can be attributed to the reduction of the capacity of the external oxygen to diffuse into the midst of the liquid medium, as a consequence of the increase in its viscosity. Reciprocally, by reason of the reduced diffusion of oxygen into the body of this medium, strict anaerobic bacteria which settle in this medium under the effect of gravity, become capable of developing in depth in this medium.

The base medium according to the invention can hence be defined as having a sufficient viscosity for strict aerobic microorganisms, even mobile, to be capable of developing only at the surface or close to the surface of this medium, this viscosity not however exceeding that which would result in too great a reduction of fluidity preventing the sedimentation of the microorganisms in the medium under the effect of gravity, and consequently the development in depth of these microorganisms, where strict anaerobic microorganisms are concerned.

This medium can also be defined as having a sufficiently great viscosity for the diffusability of external oxygen into this medium to be sufficiently reduced so that the developement or growth of strict aerobic microorganisms, introduced into this medium, can only take place at the surface or close to the latter, this viscosity not however exceeding that for which the medium would no longer possess a sufficient fluidity to enable the sedimentation under the simple effect of gravity of microorganisms introduced into the medium.

It is self-evident that in the foregoing the viscous media or viscosity agents concerned must be sterilisable, inert with respect to the microorganisms and essentially non-biodegradable, that is to say, not be liable to undergo attack on the part of bacteria, at least during the time necessary for the production and the maintenance of normally produced cultures, notably for identification or characterisation of microorganisms of the type concerned.

In one of its preferred embodiments, the medium according to the invention is a homogenous aqueous medium, transparent, containing a viscosity agent responding to the above indicated conditions and taken in suitable proportions to confer on it the above-defined viscosities.

The viscosity of the medium according to the invention is generally comprised between about 50 and about 250 centipoises (cPo). The optimum values of the viscosity are of the order of 100 to 200 cPo. In the case of a medium having thixotropic properties, the value of the viscosity to take into account is that of the medium at rest, but the measured value can be less than this by several tens of centipoises if the measurement is carried out without delay after stirring of the medium.

The agent which confers this viscosity on the medium can be in the form of a solution or a suspension in water. Its concentration is variable according to its nature. It must permit the sterilisation of the medium without destruction, by either one of the known techniques, such as heating in an autoclave or ultrafiltration. It must also preserve in water its inert properties with respect to the microorganisms. By this is meant that there must take place here neither destruction of the microorganisms, nor attack of the agent by the latter. In other words, the agent used is both non-toxic for the microorganisms, or more particularly for bacteria, and non-biodegradable.

This agent can be gelose, previously utilised as a gelling agent. The concentration of the gelose is then advantageously comprised between approximately 1.2 and approximately 1.6 g/l. A concentration of 1.4 g/l leads to a viscosity of the medium of the order of 100 cPo. It is noted in all cases that the concentration in gelose, without being negligible, is considerably less than the concentrations used conventionally for the gelling of so-called solid media.

According to other embodiments, the viscosity agent can be consitituted by any macromolecular substances, natural or synthetic, provided that they respect the requirements already mentioned relating to the sterilisation and inertness relative to microorganisms and to non-biodegradability. The soluble derivatives of cellulose such as carboxymethylcellulose may be suitable although, in certain cases, they can undergo a slow degradation under the effect of certain bacteria. Synthetic macromolecular materials which are useful are for example polyacrylamides or vinyl polymers such as polyvinyl alcohol or polyvinyl-pyrrolidone. The suitable concentrations vary according to the chemical nature of the substance and according to its molecular weight. For example, a medium of suitable viscosity is obtained by resorting, instead of and in place of gelose, to the polyacrylamide gel marketed by the Progil Company, in the proportion of about 5 g/l.

The medium according to the invention constitutes a very advantageous base medium for culture media of microorganisms in general, and more particularly for bacteria. It is remarkable and quite surprising that it has been possible to devise, in conjunction with the selection of well-defined viscosities, a single medium whose properties and whose behaviour with respect to the growth of bacteria conform at the same time to those of liquid media and to those of solid media, so well that it may be considered as "universal medium".

The medium according to the invention is a viscous medium which the presence of a viscosity agent distinguishes from conventional liquid media, the latter not being substantially more viscous than water. However, its viscosity is low, so that it remains as easy to handle and to employ as water. It is always ready for use without any special heat treatment; it is fluid and easily transferred. It is easy to introduce therein a bacterial culture and to distribute the bacteria uniformly therein by stirring, both after and before their development in the medium. It is also easy to prepare by simple solution, the most varied culture media by mixing with the base medium, nutritive substances, antibiotics, chemical compounds or generally any substance capable of having an effect on the growth of the bacteria without it being necessary that such a product whould be stable.

The same freedom in the choice of constituents is also to be found in that of the viscosity agent and it enables the use for this agent of chemical products whose purity is ensured, which is not however always the case for commerical geloses, and whose use could not in any case be considered in the case of traditional solid media.

The medium according to the invention enables it alone to identify the microorganisms, such as bacteria, by their mode of growth, as the combined employment of the different liquid and solid media would permit, but without the drawbacks inherent in the use of solid substances. With respect to the growth, for example, of aerobic and anaerobic bacteria, the base medium behaves as a solid medium, in the sense that the bacteria cannot find atmospheric oxygen in depth in the mass of the medium, by reason of the reduced diffusion of gases into this medium. On the other hand, the behaviour of the medium according to the invention is related to that of liquid media, if the movements of bacteria are considered. All bacteria, even immobile, are capable of penetrating into the medium, by sedimentation under the effect alone of gravity, but strict aerobic bacteria, even mobile, cannot multiply therein. There is observed therefore:

for strict aerobic bacteria, even mobile, a development solely at the surface or close to the latter, for aero-anaerobic bacteria, even immobile, development at the surface and in depth, for strict anaerobic bacteria, development only in depth.

To identify one type of bacteria among the three above types, it suffices to provide a culture medium constituted from the medium according to the invention, as base medium, and suitable nutrient substances and at least one transparent container, to seed it by means of a culture of said bacteria, to allow the container to stand for a sufficient time to permit appreciable development of the bacteria, and to determine where the bacteria are concentrated: at the surface of the medium and/or in depth. The final determination can be carried out by simple visual observation, or automatically, for example, by means of a densitometer or a spectrophotometer.

The medium according to the invention has the advantage of being capable of inoculation by deposition of a single drop of suspension at its surface and lends itself well to observations in series in different containers. It is also well suited for the most complex identifications of bacteria or more generally of microorganisms, bringing into action substances capable of modifying their growth characteristics, notably the mode of growth or the rate of growth. These substances can be for example, products of chemical or biological nature, in variable concentrations, substances having a growth stimulating or inhibiting action, more or less selective for certain species of bacteria, such as antibiotics, compounds containing oxygen in combined form, capable of being used by certain species of bacteria.

Another advantage of the medium according to the invention is that it facilitates quantitative measurements of the development of microorganisms. These measurements can be carried out by resorting to conventional nephelometric techniques. The operational method can be the same whatever the mode of growth of the microorganisms under study. In fact, it suffices to stir the viscous culture medium to ensure the suspension of the microorganisms which have been able to develop at the surface, so that nephelometric measurement becomes applicable to the aerobic mode of growth at the surface of the medium as well as to developments in the mass.

The medium according to the invention can be used in any containers not liable to attack by bacteria, notably of transparent plastics material, often much more practical in use than glass.

Of course, the invention relates also to the nutrient media themselves, constituted from the above-indicated base media into which are incorporated the nutriments or agents whose action on bacterial growth is to be studied, etc.

In particular, the invention relates to a culture medium retaining in the midst of the above-indicated base medium, the most essential constituents of conventional culture media, so that it can have the widest possible number of applications and be applicable in practice to the whole range of microorganisms, notably of bacteria. Among these essential constituents, are mentioned: mineral or organic sources of nitrogen, sources of carbon and of energy.

Other features of the invention will appear also in the course of the following description of examples of how the basic medium according to the invention can be used or of its application to the study of the growth characteristics of microorganisms. The examples selected will enable the very wide diversity of the possibilities of application permitted by the medium, to be appreciated.

EXAMPLE I: PREPARATION OF THE MEDIUM

A viscous medium according to the invention (unless it has been prepared in advance) is prepared, by mixing water with DIFCO gelose to a final concentration of 1.4 g/l. If necessary this medium is completed, after sterilisation, by basic nutritive substances, for example meat peptone.

It is then distributed in fractions of identical volumes in a series of similar tubes or jars. Glass test tubes can be used, but it is advantageous to use tubes of transparent plastics material, destroyed after use and of dimensions adapted to economical use of the medium. It is advantageous to use tubes of a diameter such that the surface to height ratio is of the order of 1 to 2 or of 1 to 3. For example, 2 ml of medium is placed in a tube having a 1 cm$^2$ section so that the height of the column is 2 cm.

To the different tubes chemical substances can then be added, selected according to the biological phenomena which are to be observed and a drop of a bacterial suspension to be analysed is deposited at the moment of use, at the surface of the medium, in each tube.

EXAMPLE II: STANDARDIZED METHOD FOR USING THESE MEDIA FOR ISOLATING BACTERIA.

Into 10 similar tubes borne by the same holder and containing in the same volume the same viscous medium and a nutrient substance (meat peptone), doses of sodium chloride are added, increasing from one tube to the next to obtain respective concentrations of 5 g/l, 10 g/l, 20 g/l, 40 g/l, 60 b/l 120 g/l, and 240 g/l.

These tubes are than seeded with substances assumed contaminated by several bacterial species as is frequently encountered in human pathology, in feces or in contaminated foodstuffs.

After 24 hours of undisturbed cultivation, only the species most resistant to salt is developed in the tubes containing the strongest concentrations of salt. It is thus isolated from all the others. It can be sampled at the surface and/or in depth according to the place where the development is concentrated.

According as it is developed, at the surface, or in depth, or simultaneously at the surface and in depth, a bacterium is identified as aerobic, anaerobic, or aeroanaerobic.

The replacement of sodium chloride by another inhibiting chemical substance similarly makes it possible to seek the presence of other bacteria which are selectively resistant to the substance, and to isolate them in the tube where the concentration of inhibiting substance is highest.

If the culture sampled in the last tube can still contain several bacterial species, it is used to seed another series of tubes or several successive tubes, containing different inhibitors, at doses increasing in each series, so as to isolate these species.

The whole of these operations can be programmed, their operation automatised, the results recorded on a photometer and the data processed by computer.

EXAMPLE III: BRINGING INTO EVIDENCE OF THE USE OF OXYGEN FROM NITRATE BY STRICT AEROBIC BACTERIA: FOR EXAMPLE PSEUDOMONAS AERUGINOSA 2 to 3 ml of an aqueous nutrient medium containing 1.4 g/l of DIFCO gelose and potassium nitrate in the proportion of 1 g/l are introduced in a tube having the size specified in the foregoing example.

A suspension of strict aerobic bacteria to be analysed is deposited at the surface, simply by allowing a drop to fall in by means of a pipette. The bacteria precipitate slowly in the medium.

During incubation at the selected temperature, for example 30° C., the bacteria which are capable of using oxygen from the potassium nitrate have no need for atmospheric oxygen; they can develop in the depth of the medium. The bacteria which do not use oxygen from nitrates can only develop at the surface in contact with atmospheric oxygen.

A very simple process is thus available for establishing the possible ability of a strictly aerobic bacteria to consume also oxygen form a nitrate. This enables for instance distinction to be made between *Pseudomonas aeruginosa*, which develops in the depth of the medium, and *Pseudomonas putida*, which only develops at the surface.

For aero-anaerobic bacteria, according to the same process, it is possible to replace the nitrate by potassium chlorate whose effect is opposite: in fact, the bacteria which consume oxygen for chlorate are killed by the chlorine which is thus released. Consequently, aero-anaerobic bacteria which use potassium chlorate multiply in depth but are killed, whilst those which do not use it develop normally.

EXAMPLE IV

Results similar to those of example II are obtained by using as the viscosity agent, PROGIL polyacrylamide in the concentration of 5/1000, replacing the gelose.

EXAMPLE V: NEPHELOMETRIC MEASUREMENT OF THE CONSUMPTION OF A SUBSTRATE BY A MICROORGANISM, SUCH AS A YEAST (CANDIDA ALBICANS).

A viscous medium with 1.4 g/l of gelose such as that of example I is used to study quantitatively the consumption of chemical products by yeasts. Where the chemical products are of the type which the yeast is only capable of assimilating in the presence of atmospheric oxygen, the yeast develops at the surface exclusively. In the opposite case, it develops in depth.

By observing the culture obtained, it is possible to distinguish the different species of yeasts. Thus, *Candida albicans* develops at the surface in the presence of trehalose, whilst *Candida tropicalis* is cultivated in depth in the two cases.

In all cases, the cultures are placed in suspension homogeneously, either by simple mechanical stirring of the tubes or by shaking with a steel or nickel ball moved in the medium by means of a magnet, and the development is measured by nephelometry.

In general, it is observed that the invention relates therefore both to a process for identifying microorganisms or even for separating microorganisms from a mixture containing them, having regard to their behaviour with respect to oxygen under predetermined conditions. This process is characterised in that these microorganisms or this mixture of microorganisms is seeded on the medium defined above, contained in a tube, this medium containing in addition the necessary nutriments for the establishment of the above-said predetermined development conditions, the height or the depth of the medium inside the tube being sufficient to provide, below the upper surface of the medium which is in contact with the ambient atmosphere, a level which is sufficiently isolated from the external oxygen for strictly anaerobic bacteria to be able to develop therein. It is possible then, after incubation, to collect the cultures which will have formed, possibly at different levels of the culture medium, hence the possibility of separating different sorts of microorganisms.

The conditions with which the viscosity of the culture medium must comply have been defined above. In particular, they must enable the sedimentation towards the bottom of the microorganisms deposited at the surface of the medium. This sedimentation can however be fairly slow.

According to an advantageous additional feature of the process according to the invention, it is possible to achieve more easily the seeding of said microorganisms or of said mixture of microorganisms over the whole height of the medium, by means of a solid element, notably a bead, denser than the culture medium and on which the microorganisms or mixture of microorganisms to be studied will have initially been deposited. The solid element, and preferably the bead, then constitutes a vehicle whose purpose is both to draw downwards the microorganisms introduced into the medium, thereby producing a seeding over the whole of its path through the culture medium.

Of course, the bead must be constituted from a material inert relative to the microorganisms and to the medium. It is for example, constituted of glass ceramics or of an inert plastics material. It can also be formed from an inert metal. Said material can be a porous one.

Besides the greater speed of seeding the culture medium with the microorganisms to be studied, the presence of the bead at the bottom of the tube enables it to be ensured that the seeding has really been carried out (in particular that the microorganisms to be studied do not remain stuck to the walls of the tube above the upper level of the culture medium, as can occur in the case where these microorganisms are introduced into tubes by means of a drop of water deposited on the walls of the tube with a pipette).

As is self-evident and as emerges already from the foregoing, the invention is not limited to those of its types of application and embodiments which have been more especially envisaged; it encompasses on the contrary, all modifications.

I claim:

1. A fluid medium, useful for microbiological work and for identification of a microorganism and mixtures of different microorganisms on the basis of their aerobic and nonaerobic growth properties, which medium need not be liquified by heating prior to inoculation, which is inert with respect to the microorganisms, is non-biodegradable and sterilizable without loss of its properties, which comprises as a viscosity control agent a synthetic or natural macromolecular substance selected from the group consisting of water-soluble derivatives of cellulose and water-soluble vinyl polymers, and which (1) has the properties of a liquid and is innoculatable and stirable to permit microorganisms to be distributed uniformly therein by stirring prior to or after development of the microorganism;

(2) has a viscosity so low and remains so liquid that non-motile microorganisms after innoculation onto the surface of said liquid medium, sediment to the bottom of the medium by gravity alone, said liquid property being independent of exposure to heat;

(3) has, however, such viscosity with respect to gases that diffusion of atmospheric oxygen from the surface of the medium into the body thereof is virtually nil;

(4) said liquid and viscosity properties being stable from the time of innoculum with the microorganism through the time of cultivation and identification of said microorganism; and (5) wherein said liquid and viscosity properties are such that (a) strict aerobic microorgainisms, even though motile do not multiply inside the medium, (b) strict anaerobic bacteria multiply only in the depth of the medium, and (c) aeroanaerobic bacteria, even though non-motile multiply at the surface and in the depth of the medium.

2. The fluid medium of claim 1 wherein the macromolecular substance is a water-soluble derivative of cellulose.

3. The fluid medium of claim 2 wherein the water soluble derivative of cellulose is carboxymethylcellulose.

4. The fluid medium of claim 1 wherein the macromolecular substance is a water-soluble vinyl polymer.

5. The fluid medium of claim 4 wherein the polymer is polyvinyl alcohol.

6. The fluid medium of claim 4 wherein the polymer is polyvinylpyrrolidone.

* * * * *